United States Patent [19]

Rock et al.

[11] Patent Number: 4,678,332

[45] Date of Patent: Jul. 7, 1987

[54] BROADBAND SPECTROMETER WITH FIBER OPTIC REFORMATTOR

[76] Inventors: Dan Rock, 909 Torrance; Mark Roth, 1518 Burgundy St., both of Garland, Tex. 75040; Stephen F. Sagan, 4633 Ringgold La., Plano, Tex. 75075

[21] Appl. No.: 581,950

[22] Filed: Feb. 21, 1984

[51] Int. Cl.⁴ .................................................. G01J 3/18
[52] U.S. Cl. ................................. 356/328; 350/96.25
[58] Field of Search ................ 340/632; 350/96.24, 350/96.25; 356/326, 328, 302, 305, 308, 309, 319

[56] References Cited

U.S. PATENT DOCUMENTS

| | | | |
|---|---|---|---|
| 3,457,416 | 7/1969 | Elliott | 356/328 |
| 3,885,879 | 5/1975 | Louder et al. | 356/419 |
| 3,923,399 | 12/1975 | Brumley | 356/328 |
| 4,340,303 | 7/1982 | Grisar et al. | 356/313 |
| 4,375,919 | 3/1983 | Busch | 356/328 |
| 4,487,504 | 12/1984 | Goldsmith | 356/323 |
| 4,516,832 | 5/1985 | Jain et al. | 350/96.24 |
| 4,519,707 | 5/1985 | Kuffer | 356/326 |

OTHER PUBLICATIONS

Brochure/Rank Precision Industries, Inc., 12/1971, 8 pages.

Primary Examiner—F. L. Evans
Attorney, Agent, or Firm—Richard K. Robinson; James T. Comfort; Melvin Sharp

[57] ABSTRACT

The invention provides a system having a broadband spectrometer with a fiber optic reformattor for field use in detecting and identifying gas clouds within a field of view. The system includes a grating type spectrometer, a fiber optic reformattor, a focal plane detector array and electronics for background signal subtraction techniques for generating spectral signature data which is analyzed for gas detection and outputting a decision making signal for recognition.

17 Claims, 14 Drawing Figures

BROADBAND SPECTROMETER WITH FIBER OPTIC REFORMATTOR

This invention relates to gas detection and identification systems and more particularly to a broadband spectrometer based system.

In the past three types of gas detection and identification system designs have been used to provide long range detection of toxic or undersirable gases or both. The first design is based on passive forward looking infrared (FLIR) technology coupled with a multi-element filter wheel. The second design is an active system design utilizing a laser probe to artificially stimulate a gas cloud. The third design is based on Fourier transform spectroscopy as performed with a scanning Michelson interferometer to detect the presence of gas clouds.

The passive FLIR type is disclosed in U.S. Pat. Nos. 4,363,967 issued Dec. 14, 1982 to Efkeman et al. for a "Method and Apparatus for Far Infrared Detection," and 4,280,050 issued July 21, 1981 to Callender et al. for an "Infrared Viewer and Spectral Radiometer."

The use of three spectral bandpass filters in the Chemical Warning Directional Detector allows low spectral resolution chemical agent detection for a particular filter, the entire FLIR bandpass is constrained to that filter's bandpass with a complete spectrum determined after all the filters have been used. The device works well in uncluttered environments, but has difficulty in discriminating between nerve agents and non-nerve agents in environments containing different backgrounds and numerous interferants.

The laser detection type is based on an active laser probe concept reported in articles as follows: "On Line Laser Detection of Gases" by F. C. Harbert, BA CENG.MIEZ National AICHE meeting, 1982;" "Ethylene Mass Flow Measurements with an Automatic $CO_2$ Laser Long Path Absorption System," U. Person, J. Johansson, B. Marthinsson and S. T. Eng, Dec. 15, 1982, Vol. 21, No. 24 Applied Optics, pp. 4417–4420; "Long Path Laser Monitor of Carbon Monoxide System Improvements," L. W. Chaney, D. G. Rickel, G. M. Russwurm and W. A. McClenny, Applied Optics, Vol. 18, No. 17, September, 1979, pp. 3004; "Absorption of 339 Micron Helium-Neon Laser Emission by Methane in the Atmosphere," Byron N. Edwards and Darrell E. Burch, Journal of the Optical Society of America, Vol. 55, No. 2, February, 1965, pp. 174–177; and "Battlefield Lasers Spot Chemical Clouds," High Technology Magazine, January, 1983, p. 80.

The Fourier Transform Spectroscopy, (FTS) as performed by a scanning Michelson interferometer used to detect and identify chemical nerve agents provides high speed measurement, good sensitivity and excellent spectral resolution. However, as an FTS operates on interference between wavefronts, the optical path tolerances must be kept to within fractions of the wavelengths of interest to get conclusive results. Thermal gradients, mechanical stresses and/or environmental changes could unfavorably influence FTS output. Interferometric mechanical tolerances, cryogenic cooling, excessive weight, necessary computer processing to determine the spectrum and excessive power requirements are also drawbacks to field use.

A conventional grating type spectrometer is described in U.S. Pat. No. 3,144,498 issued Aug. 11, 1964 to Nelson L. Alpert et al. for a "High Resolution Filter-Grating Spectrometer." This spectrometer includes a radiation beam forming optics for forming a radiation beam from a scene. A plurality of optical filters are positioned adjacent to the radiation beam; one of the optical filters is selected for positioning in the radiation beam for selected optical filtering. A monochromatic entrance slit receives the filtered beam and a collimator collimates the radiation therefrom.

A plurality of optical gratings are positioned adjacent to the collimated beam and a grating selector selectively positions each of the gratings in a scanning location to receive substantially the entire radiation beam. A scanner rotates in turn each selected grating through a scanning angle to generate selected radiation wavelengths from each of the plurality of gratings.

A monochromator exit slit passes the selected radiation wavelengths to a detector. The detector generates an electrical signal representative of the intensity of the impinging isolated wavelengths.

Disadvantages of the conventional grating type spectrometer are: the need for movement of the optical elements; the receipt of information only in a narrow band at a given time; and the need for large optical elements and long focal lengths for the collimating optics to provide small fields of view.

Accordingly it is an object of this invention to provide a broadband spectrometer which is substantially free of moving optical parts, compact in size, light of weight, economical, and easy to mass produce.

Another object of the invention is to provide a broadband spectrometer which receives information about the entire spectral range during an entire scan to reduce substantially the period of time for a spectral scan.

Still another object of the invention is to minimize the size and overall length of the spectrometer by decoupling the collimator's numerical aperture from the field of view to reduce the focal length of the collimating optics.

Yet another object of the invention is to provide a spectrometer having increased efficiency by reducing substantially the loss of throughput energy.

A further object of the invention is to provide a spectrometer having improved capabilities for detecting and identifying chemical nerve agents, industrial gases and medical (in vivo) applications.

Briefly stated this invention comprises a conventional grating type spectrometer miniaturized by using a fiber optic reformattor element that increases the speed of the system.

The underlying equation governing the optical parameters of a conventional spectrometer is the ratio of the entrance numerical aperture (NA) to the exit numerical aperture (NA'). This ratio is also the exit slit image height (h') to the entrance slit height (h); or also the ratio of the objective focal length (fobj.) to collimator focal length (fcol.)

$$NA/NA' = h'/h = fobj./fcol.$$

For a given field of view ($\theta$) the entrance numerical aperture is defined as:

$$NA = \text{Tan}(\theta/2)$$

In the conventional grating type spectrometer speed and field of view (FOV) are coupled. The fiber optic reformattor decouples the direct relationship between the numerical aperture and field of view. Thus, for a chosen FOV, the speed of the collimating optics increases and smaller optical elements result from a numerical aperture greater than the FOV. In addition, variable fields of view are feasible with the addition of a variable focal length collecting lens system.

In addition the use of a fiber optic reformattor element reformats the entrance slit to the spectrometer to any desired shape. The front face of the fiber optic reformattor, thus, becomes the field stop for the collecting optics. This, in turn, allows more flexibility in collecting optics design and/or field of view.

Further, the use of a focal plane detector array eliminates the need for movement of the diffraction grating or detector assembly and thereby reducing the time to achieve a completed scan.

Other objects and features of the invention will become more readily apparent from the following detailed description when read in conjunction with the accompanying drawings in which.

Figure 1:
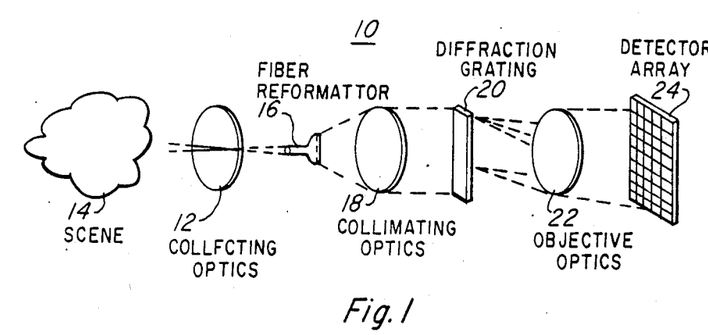
FIG. 1 is a diagrammatic view of a broadband spectrometer constituting the subject matter of this invention.

Referring now to FIG. 1, the system 10 functions as a grating type spectrometer with an "active" (laser probe) detection system or a "passive" detection system and can by suitable choices of lens elements, materials, dispersing element and detector type function at any spectral bandpass. The system 10 includes an optical channel path including a collector optics or lens system 12 (shown as a single lens) for collecting electromagnetic energy emanating from a scene 14 into a radiation beam. The scene 14 is a gas cloud or other physical items or both as will be hereinafter described.

A fiber optics reformattor 16 is positioned to receive the radiation beam of the collecting optics and to reformat the incoming energy. Thus the back face of the fiber optic reformattor becomes the source/slit for a spectrometer. A collimating optics 18 collimates the output of the fiber optics reformattor onto a dispersing element such as, for example, a diffraction grating (ruled or fiber) 20. An objective optics 22 receives the output of the diffraction grating and focuses the dispersed spectrum onto a detection plane. A film or a focal plane detector array 24 positioned at the detection plane records the spectral signature of the incoming radiation.

Figure 2:
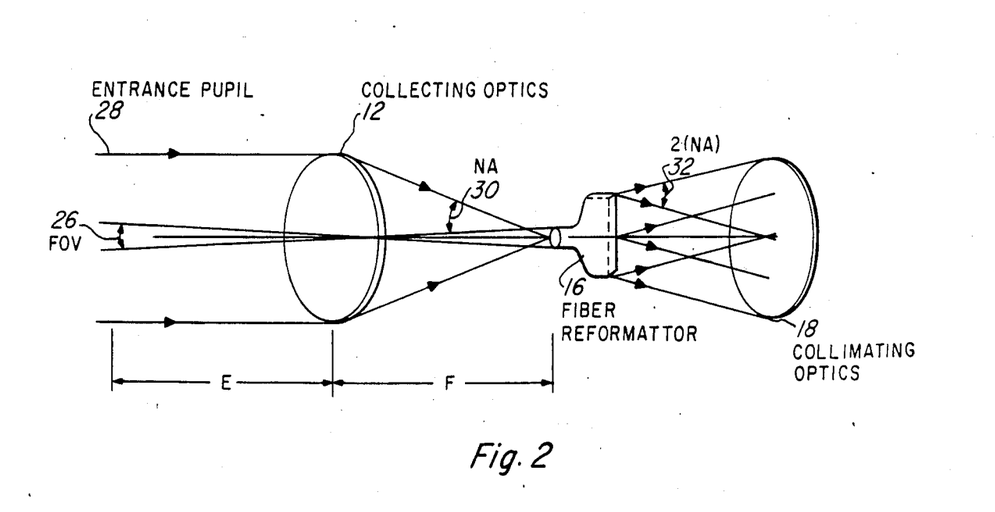
FIG. 2 is a partial diagrammatic view showing the uncoupled field of view and numerical aperture of the invention.

By using the fiber optic reformattor 16 with collecting optics 12 the collimating optics 18 numerical aperture is decoupled from the field of view as shown in FIG. 2. Thus, the focal length of the collimating optics 18 can be reduced to minimize the size and overall length of the system. The field of view 26 (FIG. 2) of this reformatted spectrometer is determined by the size and shape of the fiber optic reformattor's 16 front face, which acts as a field stop defining the field of view 26, and the focal length of the collecting optical system. The sampled field of view can be fixed or variable depending on whether the collecting optical system is of a fixed or variable focal length.

Electromagnetic energy enters the entrance pupil 28 and is focused by the collecting optics 12 onto the front surface of the fiber optics reformattor 16. The numerical aperture 30 is defined by the f/number of the collecting optics lens system. The back face of the fiber optics reformattor serves as the entrance slit to the spectrometer part of the system. Each fiber of the fiber optics reformattor has an output having a numerical aperture 32 equal to two times the numerical aperture 30 impinging on the collimating optics 18.

The most efficient operation of this spectrometer optical system occurs when the entrace pupil 28 is a telecentric pupil at the fiber reformattor. However, for a given field of view, higher energy densities on the front face of the fiber optics reformattor are achieved by increasing the numerical aperture of the collecting optics and reducing the required bundle size.

The numerical apertures of the fibers and of the optical system components and the fabrication limits of the detector plane and individual fibers ultimately determine the overall length and sizing of the elements in the system.

The ability to collect energy at one end of the fiber bundle in one geometry and reformat the fibers on the other end to another geometry is possible with a coherent or incoherent bundle.

Use of a coherent fiber optic reformattor and a two dimensional detector array allows spectral and spatial information to be collected concurrently. Coherent as used herein means that the sequential arrangement of the fibers of the fiber optics bundle is known (encoded) for corresponding sequential coupling to the focal plane array.

Figures 3A, 3B:
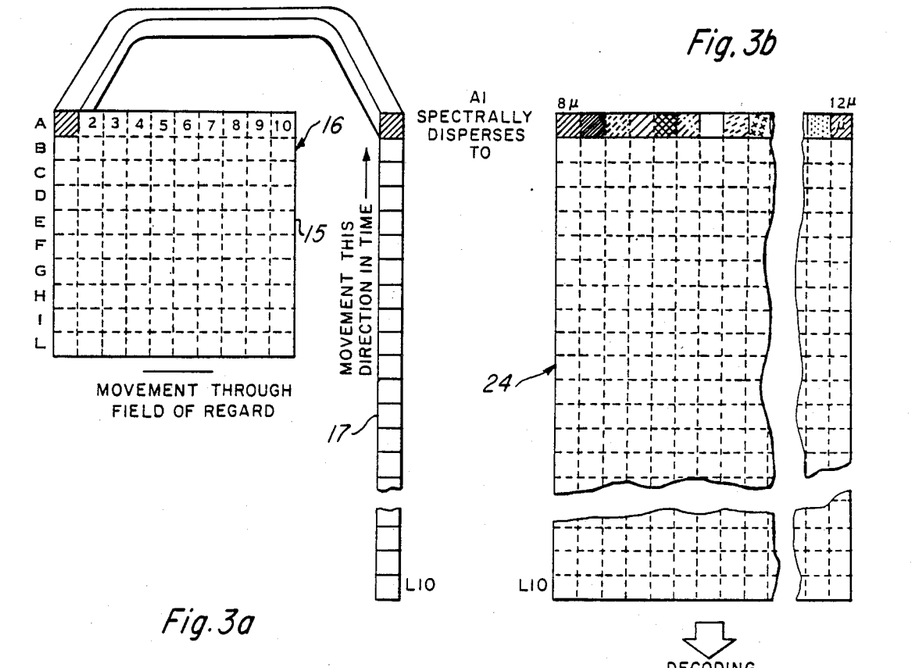
FIGS. 3a-3c are views showing an encoding sequence for a coherent fiber optic reformattor and a two dimensional detector array.

An encoding sequence for a coherent fiber optic reformattor 16 is shown in FIG. 3a. The original scene 14 falls on the front face, 15 of the fiber optic reformattor 16 (FIG. 3a) serving as a field stop. The front face ends of the fibers are arranged in an array of A-L rows and 1-10 columns and the back face 17 ends of the fibers are reformatted to a slit which serves as the entrance slit to a spectrometer. As reformatted the back face ends form a vertical slit beginning at the top with the A1 fiber and ending at the bottom with the L10 fiber.

Figure 3C:
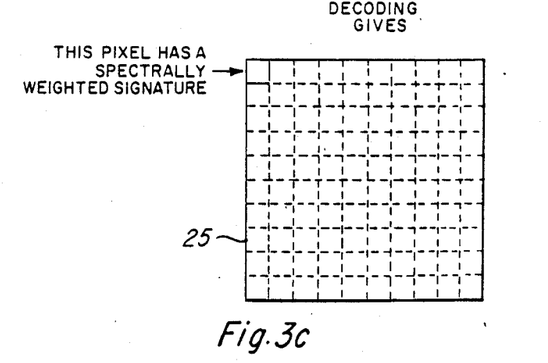

The dispersed spectrum falls on the two dimensional focal plane type detector transducer 24 (FIG. 3b) for conversion to electrical signals. The detector 24 has A1 through L10 rows of detector elements. The number of elements in each row determines the resolution between the spectral range, which as shown in FIG. 3b, is in the 8-12 micron wavelength range for each fiber optic. Upon decoding the output of the detector array an imaging spectrometer 25 (FIG. 3c) gives a map of the spectral information while keeping the spatial information; thus, regions of the scene can be identified from their spectral signatures.

In the example, the horizontal swaths through the field of view can yield spectral signatures and a map of vertical changes in the spectrum can be made as a function of the horizontal swaths vertical position. When the image falling on the field stop is reformatted coherently by the fiber bundle to a slit, a low resolution imaging system can spectrally disperse regions in a scene. The size of the pixel in the image to be spectrally resolved is determined by the signal-to-noise ratio necessary for detection in the focal plane array, which is a function of the detector spectral response and detectivity, width of the spectral bin, and integration time.

It will be appreciated by one skilled in the art that if the field of view is moved throughout a field of regard, a particular region of the scene will appear spectrally dispersed at different positions in the cross dispersion direction. Thus, by proper choice of integration time and suitable signal processing the region can be tracked and by co-adding the signals in a time delayed integration situation the signal-to-noise ratio can be increased.

Figure 4:
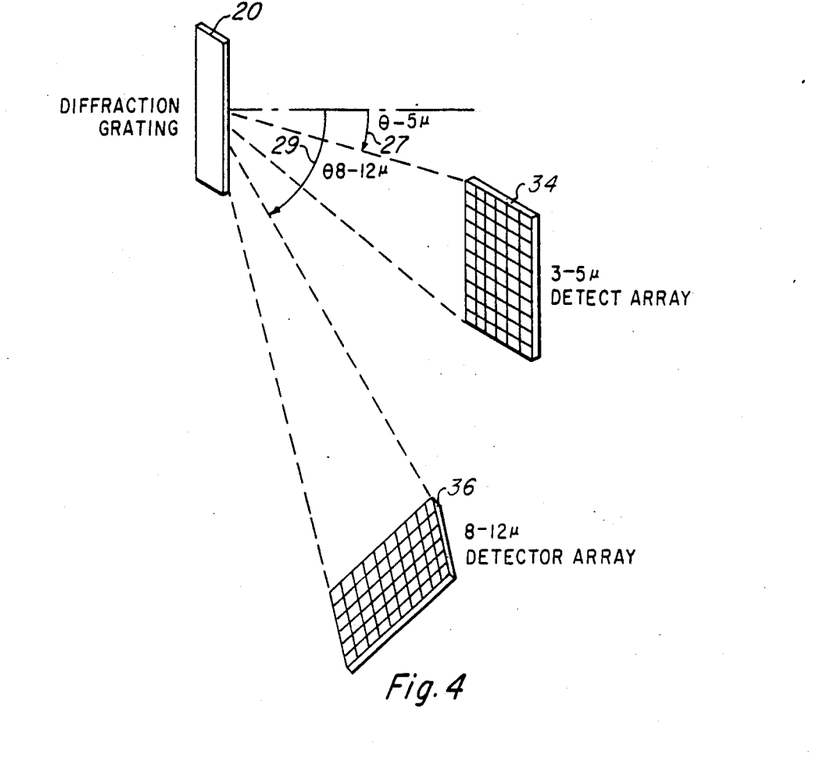
FIG. 4 is a partial diagrammatic view for a multiband spectrometer.

It will also be appreciated by one skilled in the art, that by positioning arrays 34 and 36 (FIG. 4) sensitive in the requisite spectral bandpasses (3–5 micron and 8–12 micron) at the proper diffraction angels 27 and 29 a multiband system is formed for viewing different regions in the field of view of the system.

In an incoherent embodiment knowledge of the location of the fibers in the fiber bundle is not required. Otherwise the fiber optics reformattors are similar; however, spatial information is lost. The incoherent system allows more efficient coupling of the incoming energy to the spectrometer for higher signal-to-noise ratio, faster speeds at smaller fields of view and lower integration times for focal plane detector arrays. The fiber optics reformattor 16 (FIG. 2) uses a circular front face to a slit back face to improve substantially the speed and spectral purity.

Figure 5A:
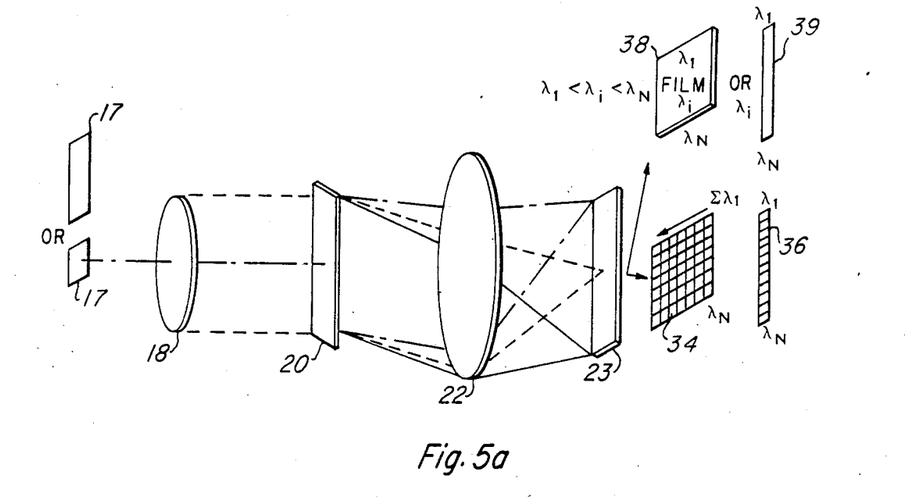
FIGS. 5a and 5b are partial diagrammatic views showing detector configurations serving as multiple slits for decreasing integration time of the spectrum and eliminating the need for any movement of the optical elements.
Figure 5B:
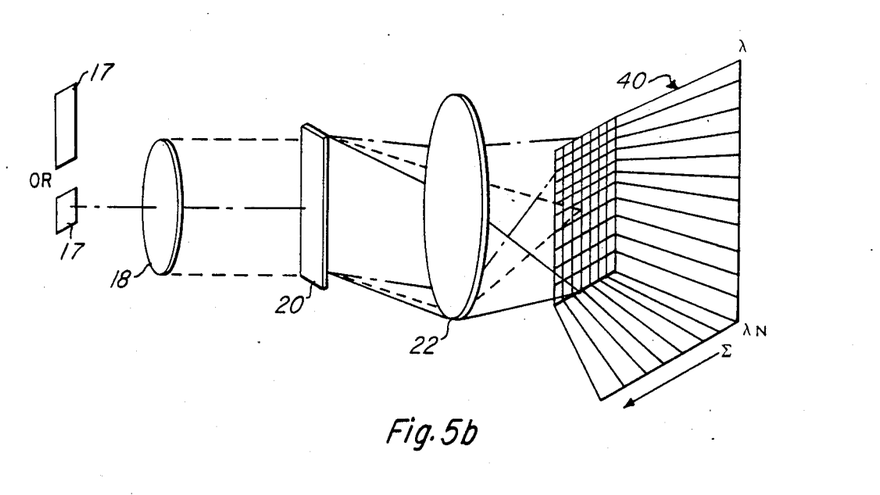

Referring to FIGS. 5a and 5b, the fiber optics reformattor 16 has its back face 17 configured either as a rectangle or square for passing the electromagnetic energy through the collimator 18, diffraction grating 20, and objective lens 22 to the detector plane 23 as a series of monochromatic slits. Either the two dimensional focal plane array 34 or the linear array 36 is selectively positioned at the detector plane 23; the selection depends on the entrance slit configuration, i.e. the two-dimensional focal plane array detector 34 is used with the reformattor slit 17 having a rectangular shaped entrance slit and the linear array detector 36 is used with a square shaped slit. Thus, with the two dimensional focal plane array detector the spectrum is detected in the columns (lambda$_1$–lambda$_N$) and each row element co-added to increase the signal-to-noise ratio for each spectral color; with the linear array detector 26' the spectrum is detected without value enhancement. The detectors 34 and 36 can be replaced with photographic films having the shapes of the detectors 34 and 36.

It will be appreciated by those skilled in the art that where there is a fabrication constraint on how small the detectors can be, a second fiber bundle 40 (FIG. 5b) can be positioned at the focal plane 23 in front of the detector array. The second fiber bundle acts as a tapered fiber magnifier (A1<A2) with thinner slit dimensions serving as exit slits of the spectrometer for improved resolution.

Figure 6:
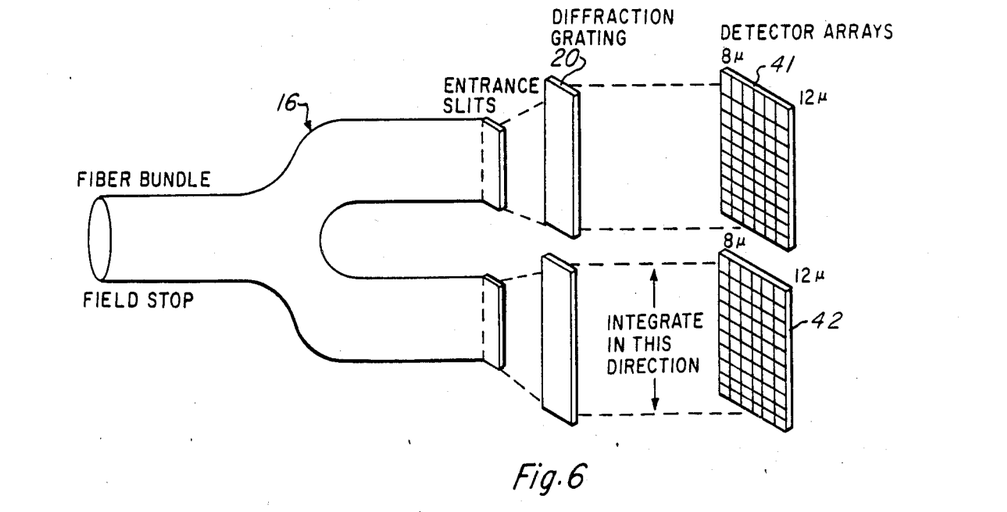
FIG. 6 is a partial diagrammatic view showing a multiple detector array configuration of the invention.

In another embodiment (FIG. 6) multiple detector arrays or transducers 41, 42 are used in conjunction with a bifurcated fiber optics reformattor 16. The detectors are positioned with their spectral bins aligned thereby increasing the height of the exit slit. Again by adding the signals of an increased area of detectors along the height of their spectral bins the signal-to-noise ratio is improved.

Figure 7:
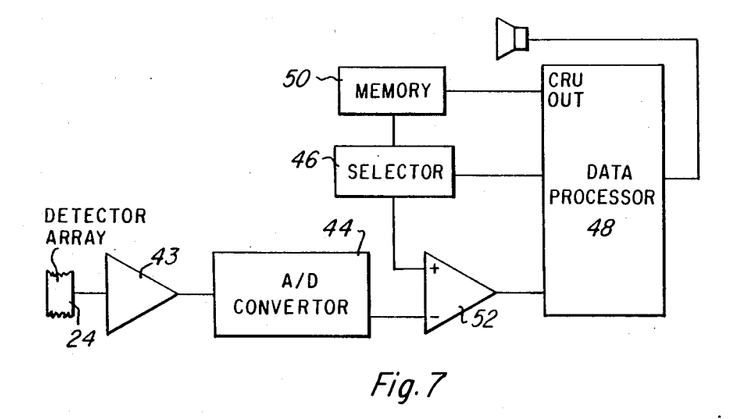
FIG. 7 is a block schematic diagram of the signal processor.

The electrical outputs of the detector array 24 elements (FIG. 7) are amplified to a working level by amplifier 42. An analog to digital converter 44 is connected to the amplifier 43 for digitizing the analog ouput of the amplifier. A selector 46 is connected to the A/D converter 44 and to the control register unit terminal of a data processor 48.

Figure 8A:
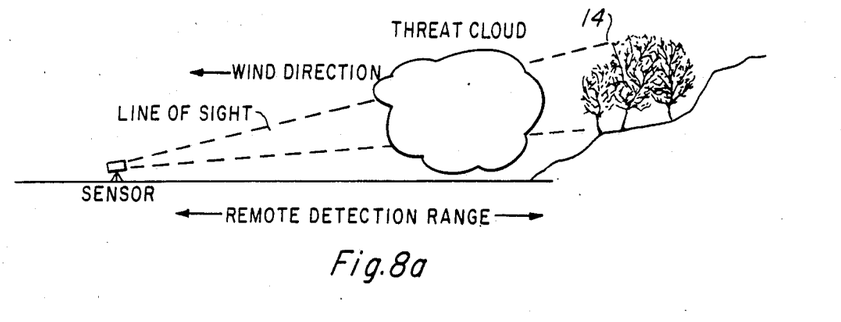
FIGS. 8a-8d constitute a view showing the operation of the broadband spectrometer and resulting signals.
Figure 8B:
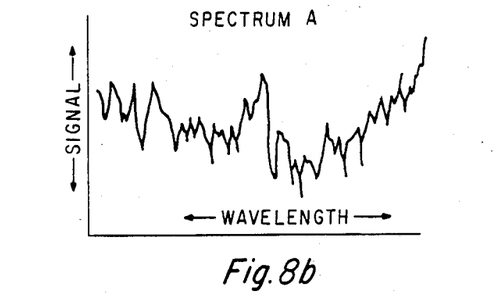
Figure 8C:
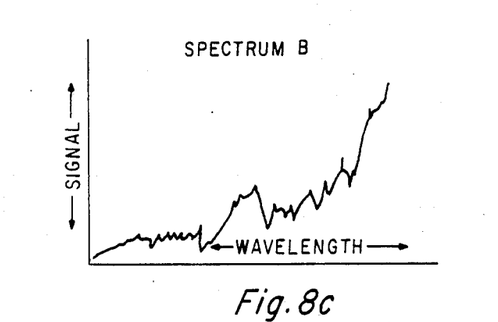
Figure 8D:
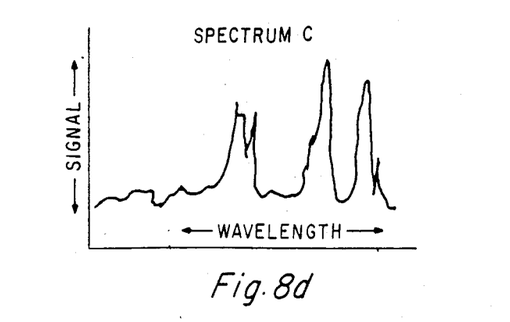

The selector 44 is controlled by the data processor, first to input digitized signals for a background spectrum of the scene 14 containing no interferent (FIG. 8c) into memory 50 and secondly to input these signals into a comparator 52 for comparison with currently detected digitized signals containing an interferer (FIG. 8b) in the scene 14 (FIG. 8a). The data processor 48 is connected to the comparator for receiving the extracted spectrum of the interferent (FIG. 8d) and matching the extracted spectrum to known spectra contained in its memory and a decision made for subsequent device action such as, for example, sounding an alarm.

Although preferred embodiments of the present invention have been described in detail, it is to be understood that various changes, substitutions, and alterations can be made therein without departing from the scope of the invention as defined by the appended claims.

What is claimed is:

1. A broadband spectrometer apparatus for field use comprising:
    (a) a spectrometer means for dispersing radiation into its component wavelengths including: a collecting optics having a first numerical aperture for collecting electromagnetic energy and for focusing the collected electromagnetic energy according to the first numerical aperture, a fiber optics reformattor having a plurality of fibers arranged to form a front face forming a field stop for receiving the focused electromagnetic energy and a back face forming an entrance slit for the spectrometer means, and each single fiber optic of the plurality of fiber optics at the back face has a second numerical aperture having a mathematical relation to the first numerical aperture such that a value for the second numerical aperture is larger than the value of the first numerical aperture, the fiber optics reformattor being for reformatting the received and focused electromagnetic energy and a means for dispersing the focused and reformatted electromagnetic energy into component wavelengths; and
    (b) detector means operatively connected to the spectrometer means for detecting the reformatted, received, dispersed and focused electromagnetic energy to obtain the dispersed radiation component wavelength thereby.

2. The broadband spectrometer apparatus according to claim 1 wherein the means for dispersing includes a ruled diffraction grating.

3. A broadband spectrometer apparatus comprising:
    (a) a collecting optics means for viewing a scene radiating electromagnetic energy and forming the electromagnetic energy into a beam;
    (b) a fiber optics reformattor means operatively positioned for receiving the beam of electromagnetic energy and decoupling the direct relationship between the numerical aperture and field of view, the reformattor means having first and second ends formatted to form, respectively, a field stop and a spectrometer entrance slit;

(c) a collimating optics means operatively positioned for receiving and collimating the reformatted beam;

(d) a diffraction grating means operatively positioned for receiving the collimated beam and converting the beam to a dispersed spectrum;

(e) an objective optics operatively positioned for receiving the dispersed spectrum and focusing the dispersed spectrum onto a detection plane; and (f) a detector means positioned at the detection plane for detecting the dispersed spectrum.

4. A broadband spectrometer apparatus according to claim 3 wherein the detector means is a film for recording the dispersed spectrum.

5. A broadband spectrometer apparatus according to claim 3 wherein the detector means is an array of detector transducers for generating electrical signals proportional to the intensity of the electromagnetic energy impinging thereon.

6. A broadband spectrometer apparatus according to claim 5 wherein the array of detector transducers is a two dimensional focal plane array and the optical elements of the apparatus are stationary.

7. A broadband spectrometer apparatus according to claim 3 wherein the fiber optics reformattor comprises a fiber optics bundle.

8. A broadband spectrometer apparatus according to claim 7 wherein the fiber optics bundle is a coherent bundle.

9. A broadband spectrometer apparatus according to claim 7 wherein the fiber optics bundle is a coherent bundle and the detector means is a two-dimensional focal plane array whereby the spectral and spatial information is preserved.

10. A broadband spectrometer apparatus according to claim 7 wherein the fiber optics bundle is either a coherent or an incoherent bundle and the detector means includes a plurality of detector arrays sensitive in a preselected spectral bandpass and positioned at preselected diffraction areas for producing a multiband system.

11. A broadband spectrometer apparatus according to claim 7 wherein the fiber optics bundle is an incoherent bundle for increased efficient coupling of the incoming energy and faster speeds at smaller fields of view.

12. A broadband spectrometer apparatus according to claim 11 wherein the detector means is a focal plane detector array for lower integration times.

13. A broadband spectrometer apparatus according to claim 3 wherein the fiber optics reformattor comprises a bifurcated fiber optics bundle and the detector means comprises a plurality of detector arrays positioned to align their spectral bins for increasing substantially the height of the entrance slit.

14. A broadband spectrometer apparatus according to claim 13 including a means for adding the signals of the detectors along the height of their spectral bins for improving the signal-to-noise ratio.

15. A broadband spectrometer apparatus according to claim 3 further including a signal output processing means operatively connected to the detector means for selectively determining the presence and absence of interferents.

16. A broadband spectrometer apparatus according to claim 15 wherein the signal output processing means includes an amplifier means operatively connected to the detector means for amplifying the output of the detectors, an analog to digital converter for digitizing the amplified detector signals, a comparator means for comparing stored background spectrums and real time spectrums and providing a difference spectrum, a data processing means for identifying interferents and selectively outputting warning signals, and an alarm means operatively connected to the data processing means for receiving any warning signals and activating the alarm means.

17. A broadband spectrometer apparatus according to claim 3 further including an array of tapered fiber optics positioned to receive the spectrum output of the diffraction grating means and magnifying the spectrum output for the detector means to increase the resolution.

* * * * *